United States Patent
Schwarz et al.

(10) Patent No.: US 8,029,283 B2
(45) Date of Patent: *Oct. 4, 2011

(54) ABUTMENT WITH A HYDROXYLATED SURFACE

(75) Inventors: Frank Schwarz, Dusseldorf (DE); Jürgen Becker, Dusseldorf (DE); Marco Wieland, Basel (CH); Michel Dard, Liestal (CH)

(73) Assignee: Straumann Holding AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 11/680,042

(22) Filed: Feb. 28, 2007

(65) Prior Publication Data

US 2007/0202462 A1 Aug. 30, 2007

(30) Foreign Application Priority Data

Feb. 28, 2006 (EP) .................................. 06004061

(51) Int. Cl.
*A61C 8/00* (2006.01)
(52) U.S. Cl. ......................................................... 433/173
(58) Field of Classification Search .......... 433/172–174, 433/18, 201.1; 623/23.55, 16.11, 23.53; 424/50
See application file for complete search history.

(56) References Cited

U.S. PATENT DOCUMENTS

| | | | |
|---|---|---|---|
| 3,797,113 A * | 3/1974 | Brainin .......................... 433/173 |
| 4,955,536 A | 9/1990 | Foller |
| 4,995,553 A | 2/1991 | Foller |
| 5,571,017 A * | 11/1996 | Niznick ......................... 433/174 |
| 6,527,554 B2 * | 3/2003 | Hurson et al. ................. 433/173 |
| 6,702,855 B1 * | 3/2004 | Steinemann et al. ........ 623/23.53 |
| 7,087,085 B2 * | 8/2006 | Steinemann et al. ........ 623/23.55 |
| 2003/0176927 A1 * | 9/2003 | Steinemann et al. ........ 623/23.55 |
| 2005/0064007 A1 | 3/2005 | Steinemann et al. |
| 2005/0106534 A1 * | 5/2005 | Gahlert .......................... 433/173 |

FOREIGN PATENT DOCUMENTS

| | | |
|---|---|---|
| FR | 2623709 | 6/1989 |
| FR | 2636709 | 3/1990 |
| WO | WO 00/44305 | 8/2000 |
| WO | WO 03/039390 | 5/2003 |

OTHER PUBLICATIONS

Bornstein, Michael M; Valderrama, Pilar; Jones, Archie; Wilson, Thomas; Seibl, Reinhart; Cochran, David. "Bone apposition around two different sandblasted and acid etched titanium implant surfaces: a histomorphometric study in canine mandibles." 2008, Clinical Oral Implant Res, pp. 233-241.*

European Search Report dated Jul. 31, 2006 from priority application EP06004061.

(Continued)

*Primary Examiner* — Ralph Lewis
(74) *Attorney, Agent, or Firm* — Rissman Hendricks & Oliverio, LLP

(57) ABSTRACT

Abutment of a dental implant system, having at the top a support region intended for receiving a prosthetic build-up construction and at the bottom an implant contact region intended for insertion into a receiving hole of an implant, and wherein the abutment has between the support region and the implant contact region a soft tissue contact surface. The soft tissue contact surface is at least partially hydroxylated or silanated.

9 Claims, 3 Drawing Sheets

OTHER PUBLICATIONS

Meyer, M., "Hydroxylapatitbeschichtung fur perkutane Silicon—und Titanimplantate", TU Berlin, Sep. 22, 2003 (date according to www.archive.org); URL: http://www.2.tu-berlin.de/fb6/keramik/picture/forschung/HAP/HAP.pdf. This document was cited in a corresponding EP application. Also enclosed is an English Translation of the title and a short abstract of the document (in English) prepared by applicant's EP counsel.

* cited by examiner

ABUTMENT WITH A HYDROXYLATED SURFACE

PRIORITY APPLICATION

The present application claims priority to European Patent Office Application 06004061.5 filed Feb. 28, 2006.

FIELD OF THE INVENTION

The present invention relates to an abutment of a dental implant system, said abutment having at the top a support region intended for receiving a prosthetic build-up construction and at the bottom an implant contact region intended for insertion into a receiving hole of an implant which is submerged at bone level, wherein said abutment comprises between the support region and the implant contact region a soft tissue contact surface.

BACKGROUND

Implants which are used for insertion into bone, for example for attachment of artificial teeth, are known per se. Different types of implant systems are known, for example two-part implant systems. Said two-part implant systems comprise first an anchoring part for anchoring within the bone and second an abutment. Onto the abutment prosthesis elements, such as bridges or crowns, are screwed or cemented.

Further implant systems comprising an anchoring part and an abutment are known, wherein the anchoring part of the implant system is submerged at bone level (so called submerged implants) so that the connection between anchoring part and abutment is at the marginal bone level. The term "at bone level" includes minor deviations from this level (e.g. 1 mm above or below said level). In any case, the anchoring part does not extend substantially above bone level. Said implant systems are favoured by patients due to their aesthetic advantages. However, the abutment of such implant system is in contact with soft tissue, and therefore it is important to establish an effective seal between oral environment and the endosseous part of the dental implant system.

A central property of dental implants is their osteointegration time, that is to say the time that passes before the bone substance has become connected with sufficient strength and permanently to the bone contact surface, that is to say has become integrated with it.

Therefore, much effort has been made in order to improve the osteointegration of said implants, such as described in EP 1 150 620. It was shown that the osteointegration time was significantly shorter if the bone contact surface of the implant is roughened, and in particular additionally hydroxylated and hydrophilic.

However, there is considerable evidence supporting the view that the supracrestal connective tissue plays a fundamental role in establishing an effective seal between the oral environment and the endosseous part of a dental implant. Indeed, the presence of bacteria on the implant surface or on the abutment surface may lead to an inflammation of the peri-implant mucosa, and, if left untreated, the inflammation spreads apically and results in bone resorption.

Biomaterials, 2005; 26(4): 373-81 discloses the influence of surface topography of ceramic abutments on the attachment and proliferation of human oral fibroblasts. It was shown, that polished surfaces had significantly higher percentages of initial cell attachment than the other surfaces.

J. Clin. Periodontol. 2002, 29 (5): 456-fl describes soft tissue reactions to plague formation at abutments with different surface topography. It was shown that different surface characteristics of abutments made of titanium failed to influence plague formation and the establishment of inflammatory cell lesions in the periimplant mucosa.

Different types of abutments for two-part implants are known in the art. U.S. Pat. No. 6,663,388 discloses a straight or an angular abutment which can be established by means of a base screw and a supporting ring.

U.S. Pat. No. 5,417,568 discloses an abutment for an implant of a dental prosthesis which is contoured to follow the to gingival margin. Said abutment can be fabricated from gold alloy, titanium alloy, or ceramic material. The surface of said abutment has not been treated.

U.S. Pat. No. 6,951,460 relates to an implant system including an abutment, an abutment replica and an impression coping. The abutments are intended to be connected to submerged implants.

It is the problem of the present invention to provide an abutment with improved soft tissue integration for a two part implant system, wherein the anchoring part of the implant system is submerged at bone level.

SUMMARY OF THE INVENTION

An abutment according to the invention has at the top a support region intended for receiving a prosthetic build-up construction and at the bottom an implant contact region intended for insertion into a receiving hole of an implant. The abutment has a soft tissue contact surface between the support region and the implant contact region. The soft tissue contact surface is at least partially hydroxylated or silanated, thus having the potential to promote formation of soft tissue attachment. The abutment according to the present invention is used in two-part implant systems, wherein the anchoring part of the implant system is submerged at bone level. In contrast to conventional abutments having a smooth unhydroxylated soft tissue contact surface, the abutment according to the present invention leads to the formation of new connective tissue adjacent to the soft tissue contact surface of the abutment and the new connective tissue tends to be in close contact with the soft tissue contact surface of the abutment. The loose connective tissue seems to become organized and replaced by newly formed collagen fibers, originated from its outer zone. These fibers tend to be organized in a perpendicular way towards the soft tissue contact surface, similarly to the naturally occurring fibers most responsible for compensating forces on the tooth.

An implant in terms of the present invention is intended to mean the anchor part of a two-part implant system, that is that part which becomes integrated with the bone. Said anchoring part is sunk at bone level. As mentioned before the term at "bone level" includes minor deviations from this level (e.g. 1 mm above or below said level). In any case, the anchoring part does not extend substantially above bone level.

Soft tissue contact surface in terms of the present invention is intended to mean that part of the abutment which is in direct contact with the soft tissue. In other words that part of the abutment which is not intended to be covered by the prosthetic build-up construction and is not intended to be placed in the receiving hole of the anchoring part or on the shoulder of the implant.

Hydroxylated in terms of the present invention means hydroxyl groups which are present in the outermost atomic layer of the abutment surface. If the abutment comprises titanium, zirconium, tantalum, niobium, hafnium or alloys thereof as well as chemically similarly reacting alloys, it is assumed that the surface of metal oxidizes spontaneously in air and water and that a reaction then takes place with water on the surface to form hydroxyl groups. This surface containing hydroxyl groups is referred to in the literature as a "hydroxylated" surface; cf. H. P. Boehm, Acidic and Basic Properties of Hydroxylated Metal Oxide Surfaces, Discussions Faraday Society, vol. 52, 1971, pp. 264-275. The same applies to ceramic surfaces (either on a ceramic abutment or a metallic abutment with a ceramic coating). A metal surface whose hydroxyl groups are covalently blocked, e.g. because of chemical modification, is not a "hydroxylated" surface in terms of the present invention.

Silanated in terms of the present invention means that the abutment surface or at least the soft tissue contact surface is covered by a silanole or by an organo silane compound which has at least one free hydroxyl group. Examples of such organo silane compounds are $X_n SiR_{4-n}$, wherein X is selected from the group consisting of Cl, Br, I, F or OR, and R is selected from the group consisting of lower alkyl groups, such as methyl, ethyl, propyl etc. Abutments made of metals are preferably covered by silanole, whereas abutments made of ceramic are preferably covered by an organo silane compound. Abutments made of metals can also covered by an organo silane compound and abutments made of ceramic can also be covered by silanole.

In a preferred embodiment of the present invention the soft tissue contact surface of the abutment is completely hydroxylated. Such an abutment showed good results in vivo and said abutments are economically interesting. The abutments according to the present invention have an improved soft tissue integration due to their purity (meaning that the soft tissue contact surface is free of organic compounds and the surface charge is better available). Therefore they do not bear the risk of autoimmune reactions and other unwanted side effects.

In a further embodiment of the present invention the soft tissue contact surface is roughened and hydroxylated. A roughened surface in terms of the present invention means a macroscopic texture of the surface which is obtained for example by sandblasting the soft tissue contact surface. It has been found that if the soft tissue contact surface is roughened and hydroxylated the blood coagulum is stabilized which accelerates the healing procedure.

In a further embodiment of the present invention the surface roughness of the soft tissue contact surface increases towards the support region continuously or stepwise. This means that at the upper end of the soft tissue contact surface towards the support region, the soft tissue contact surface is smooth or only slightly roughened. Said surface roughness increases towards the support region continuously or stepwise until the surface roughness of the implant to which the abutment is connected is reached.

In a further embodiment of the present invention the soft tissue contact surface is smooth but hydroxylated. A smooth surface in terms of the present invention means a macroscopic texture of the surface which is obtained for example by machining or additional polishing, preferably by electropolishing the soft tissue contact surface. With a smooth surface the accumulation of plaque can be prevented or at least minimized, and such a smooth but so hydroxylated soft tissue contact surface has outstanding wettability properties which is highly preferred.

In a further preferred embodiment of the present invention the soft tissue contact surface is hydrophilic. In terms of the present invention, the soft tissue contact surface is referred to as "hydrophilic" if it is freely accessible to the body fluid and not covered with foreign substances, for example substances with a hydrophobic action. Various volatile hydrocarbons are conventionally present in non-purified air. These are rapidly adsorbed in a thin layer by hydroxylated and hydrophilic surfaces, whereafter such surfaces are no longer hydrophilic. Likewise, such a hydroxylated and hydrophilic surface can become hydrophobic if the hydroxyl groups present on the surface associate or react chemically e.g. with carbon dioxide present in the air or with organic solvents, such as methanol or acetone, introduced via the cleaning process. The hydrophilic properties of the soft tissue contact surface may result in a higher wettability when compared to an untreated soft tissue contact surface, which promotes formation of the soft tissue. Further, the charge on the surface is better available which may accelerate the formation of soft tissue attachment as well.

In one embodiment of the present invention the abutments comprise mainly a metal selected from the group consisting of titanium, zirconium, niobium, hafnium or tantalum, preferably titanium or zirconium. Alternatively the abutments comprise an alloy of metals selected from the group consisting of titanium, zirconium, niobium, hafnium or tantalum, preferably a binary titanium/zirconium alloy. Such abutments, their nature and the metal materials used to produce them are known per se. Alternatively, the abutment according to the present invention may comprise ceramic. Such ceramic abutments comprise typically zirconia, aluminia, silica or mixtures thereof with further constituents, preferably they are made of zirconia. The cubic structure of zirconium oxide (zirconia) may be stabilized by metallic oxides at room temperature. Preferred metallic oxides are magnesium oxide, calcium oxide, oxides of the lanthanide group, preferably yttrium oxide. Depending on the content of said metallic oxides the cubic high temperature phase of zirconia can be stabilized fully or partly at room temperature (cubic stabilized zirconium oxide). Preferably zirconia is stabilized by yttrium oxide. In a further embodiment the abutment is made of a metal and is covered by a ceramic layer.

The present invention also relates to the process for preparing the above disclosed abutment.

To obtain the hydroxylated surface, the soft tissue contact surface of the abutment is preferably etched with an inorganic acid, an inorganic base, a mixture of inorganic bases or a mixture of inorganic acids. Particularly preferred are inorganic acids such as hydrofluoric acid, hydrochloric acid, sulfuric acid, nitric acid or a mixture of such acids. Preferably the abutment is etched with a mixture of hydrochloric acid (conc.), sulfuric acid (conc.) and water in a weight ratio of about 2:1:1. Alternatively the surface is activated with hydrochloric acid (conc.), hydrogen peroxide (conc.) and water in a weight ratio of about 1:1:5. The soft tissue contact surface is then washed with pure water in an inert atmosphere.

A roughened soft tissue contact surface can be obtained by sandblasting said surface and keeping the surface in the resulting state if it is already hydroxylated and hydrophilic or converting the sandblasted surface to a hydroxylated and hydrophilic state in a separate process step.

In particular, the roughened soft tissue contact surface can be produced by shot peening or sandblasting said surface and/or roughening it by using plasma technology, and then treating the mechanically roughened surface by an electrolytic or chemical process until a hydroxylated and hydrophilic surface is formed.

The preferred procedure is to
 shot-peen the soft tissue contact surface of the abutment and then etch it with diluted hydrofluoric acid at room temperature; or
 sandblast the soft tissue contact surface of the abutment, e.g. with aluminium oxide particles having a mean size of 0.1-0.25 mm or 0.25-0.5 mm, and then treat it at elevated temperature with a hydrochloric acid/sulfuric acid mixture and wash it with pure distilled and carbon-free ($CO_2$ and other carbons) water; or sandblast the soft tissue contact surface of the abutment with coarse particles, e.g. with a mixture of particles as defined above, and then treat it with a hydrochloric acid/nitric acid mixture and wash it with pure distilled and carbon-free ($CO_2$ and other carbons) water; or treat the soft tissue contact surface of the abutment with a mixture of hydrochloric acid (conc.), hydrogen peroxide (conc.) and water in a weight ratio of about 1:1:5 and wash it with pure distilled and carbon-free ($CO_2$ and other carbons) water; or roughen the soft tissue contact surface of the abutment by using plasma technology and then hydroxylate it in a mixture of hydrochloric acid (conc.), hydrogen peroxide (conc.) and water in a weight ratio of about 1:1:5 and wash it with pure distilled and carbon-free ($CO_2$ and other carbons) water; or treat the soft tissue contact surface of the abutment by an electrolytic process, optionally after mechanical roughening of the surface, and then wash it with pure distilled and carbon-free ($CO_2$ and other carbons) water; or treat the soft tissue contact surface of the abutment by plasma cleaning or UV-treatment.

These methods are known to those skilled in the art and are described for example in U.S. Pat. No. 5,071,351 and can also be applied to abutments. The hydroxylated soft tissue contact surface of the abutment is after such a treatment free of organic debris and has an increased wettability. As a result, the abutment becomes more intimately involved with the surrounding tissue structure.

Whatever the case may be, according to the invention the abutment is not subjected to further aftertreatment, i.e. it is not treated with alcohol, acetone or any other organic solvent. In particular, said pure water contains neither carbon dioxide nor hydrocarbon vapours and especially no acetone and no alcohols like methanol or ethanol. However, it can contain special additives as described below. The "pure" water used for washing has preferably been distilled several times or prepared by reverse osmosis; the water has preferably been prepared in an inert atmosphere, i.e. under reduced pressure in a nitrogen or noble gas atmosphere, for example.

Following these procedures, the abutment obtained is left in pure water and stored in a closed vessel or a covering. In addition to water, the interior of the covering can contain inert gases, for example nitrogen, oxygen or a noble gas such as argon. The abutment obtained is preferably stored in pure water optionally containing selective additives, and in a covering which is practically impermeable to gases and liquids, especially to carbon oxides, the interior of the covering being devoid of any compounds capable of impairing the activity of the implant surface.

Alternatively, the abutment could be placed in an inert gas atmosphere.

The abutment according to the invention is preferably sealed in a gas-tight and liquid-tight covering, the interior of the covering being devoid of any compounds capable of impairing the biological activity of the abutment surface. In this way it is avoided that the surface loses its activation fully or partially by means of air constituents, before the abutment is applied. In a preferred embodiment there is a reducing atmosphere in the interior of the covering. This gas-tight and liquid-tight covering is preferably a heat-sealed ampoule made of glass, metal, a synthetic polymer or some other gas-tight and liquid-tight material, or a combination of these materials. The metal preferably takes the form of a thin sheet, it being possible for polymeric materials and metal sheets, as well as glass, to be combined together to form a suitable packaging in a manner known per se.

Examples of suitable additives which can be incorporated in the pure water are cations and anions which already occur in the body fluid. In order to stabilize the positive charge the abutment according to the present invention is preferably stored at a pH ranging from pH 3 to 7, preferably 4 to 6. Alternatively it is also possible to store the abutment at a pH ranging from pH 7 to 10 in order to stabilize the negative charge. Preferred cations are $Na^+$, $K^+$, $Mg^{2+}$ and $Ca^{2+}$. The preferred anion is $Cl^-$. The total amount of said cations or anions ranges preferably from about 50 mM to 250 mM, particularly preferably from about 100 mM to 200 mM, and is preferably about 150 mM. If the covering contains divalent cations, especially Me, $Ca^{2+}$, $Sr^{2+}$ and/or $Mn^{2+}$, on their own or in combination with the above-mentioned monovalent cations, the total amount of divalent cations present preferably ranges from 1 mM to 20 mM.

The invention is explained below on the basis of figures and illustrative embodiments, without in any way limiting the invention to the embodiments shown.

DETAILED DESCRIPTION

Figure 1:
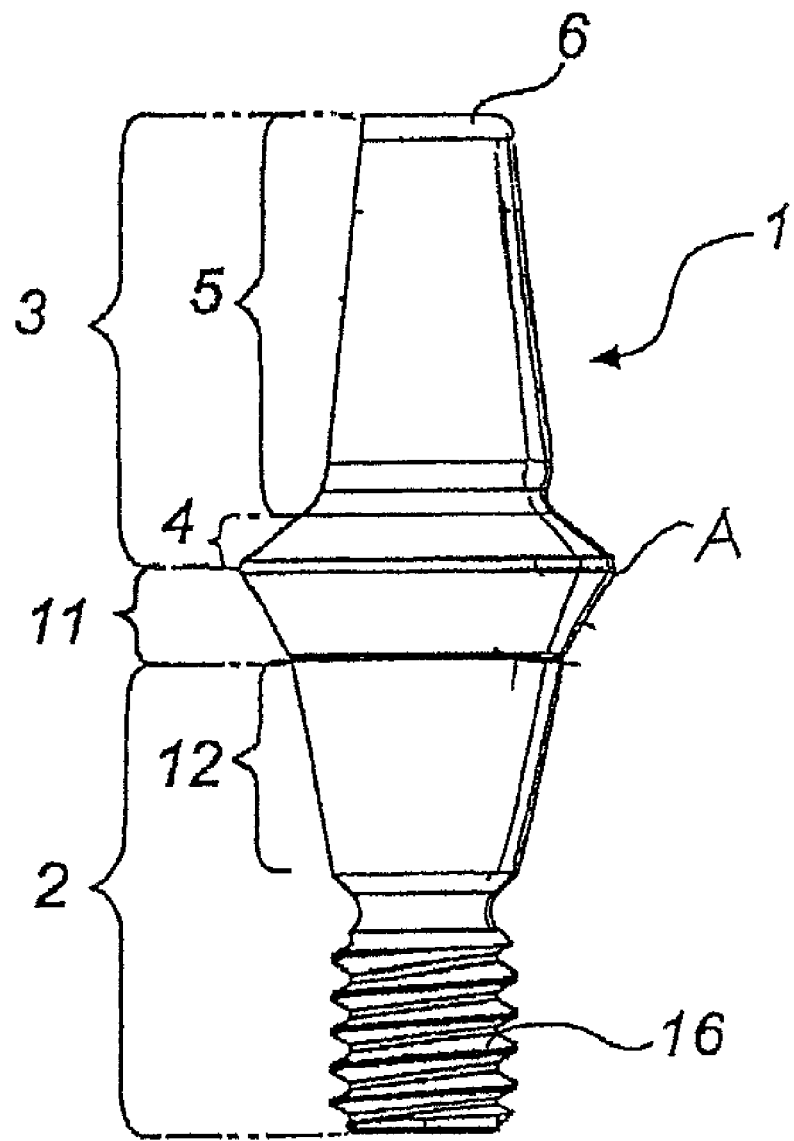
FIG. 1 is a perspective view of a first embodiment of an abutment.

FIG. 1 shows one embodiment of an abutment 1 for receiving a prosthetic build-up construction. The abutment comprises an implant contacting region 2 for connection to an anchoring part of an implant system (see FIG. 3) and a support region 3, extending coronally of said implant contacting region 2, for connection of a prosthetic build up construction thereto. The abutment 1 may be made of titanium, zirconium, tantalum, niobium, hafnium or alloys thereof or of ceramic such as zirconium oxide and the like, or a ceramic coating on a metal abutment. The support region 3 extends coronally from a maximum diameter A to a coronal end 6. The maximum diameter A of the support region is in this case coinciding with the maximum diameter of the abutment as a whole. The support region 3 comprises in this first embodiment a shoulder portion 4 and a post portion 5, extending coronally from said shoulder portion.

Between the support region 3 and the implant contacting region 2 the abutment 1 has a soft tissue contact surface 11, serving to increase the height with which the abutment 1 is extending over the implant when installed thereto. Since the implant is submerged at bone level, the soft tissue contact surface 11 extends through gingival tissue. Said soft tissue contact surface 11 is at least partially, preferably completely hydroxylated or silanated. It may be smooth, for example obtained by electropolishing, or alternatively roughened, for example obtained by sandblasting. Preferably the soft tissue contact surface is also hydrophilic in order to ensure an optimal soft tissue integration.

The implant contacting region 2 comprises a coronal contact portion 12 and a threaded shaft 16. The implant contacting region 2 is thereby adapted for connection to an implant having a conical coronal opening and being provided with internal threads for at of an abutment 1. The conical shape of the implant contacting region 2 and the implant opening, respectively, is particularly advantageous since it may be adapted to give rise to a conical seal when the implant and the abutment are screwed together.

Figure 2:
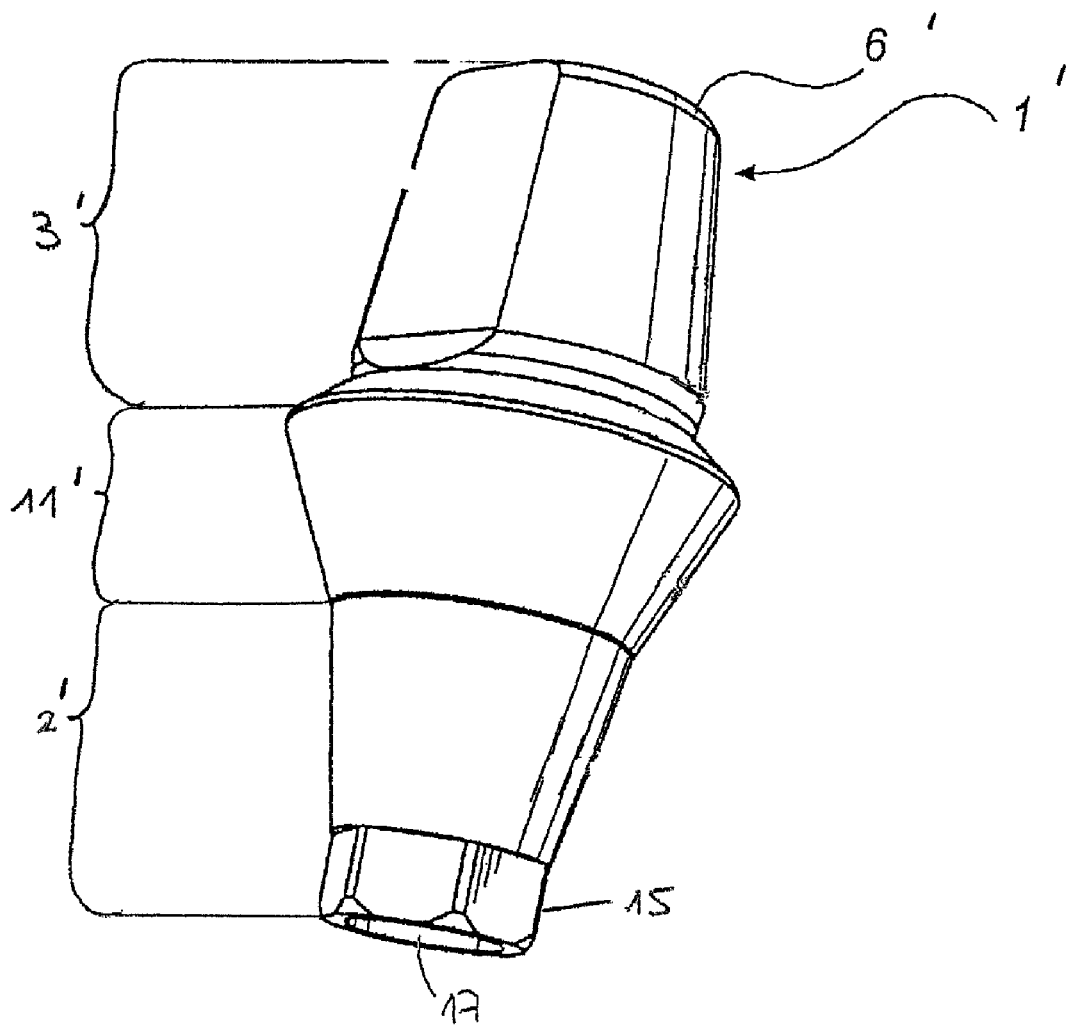
FIG. 2 is a perspective view of a second embodiment of an abutment.

FIG. 2 is a perspective view of a second embodiment of an abutment. The second embodiment differs from the first embodiment in that the implant contacting region 2' is not provided with a threaded shaft 16. Instead, it has a hexagonal locking structure 15 for rotational locking to an implant. The abutment 1' is further provided with a through bore 17 having an internal ledge. A screw may be inserted in the through bore 17, seating the screw head on the ledge, for connection of the abutment 1' to an implant. The support region 3' extends coronally from a maximum diameter of the abutment to a coronal end 6'. Also this abutment is provided with a soft tissue contact surface 11' between the support region 3' and the implant contacting region 2'. Said soft tissue contact surface 11' is at least partially, preferably completely hydroxylated or silanated. It may be smooth, for example obtained by electropolishing, or alternatively roughened, for example obtained by sandblasting. Preferably the soft tissue contact surface is also hydrophilic in order to ensure an optimal soft tissue integration.

Figure 3:
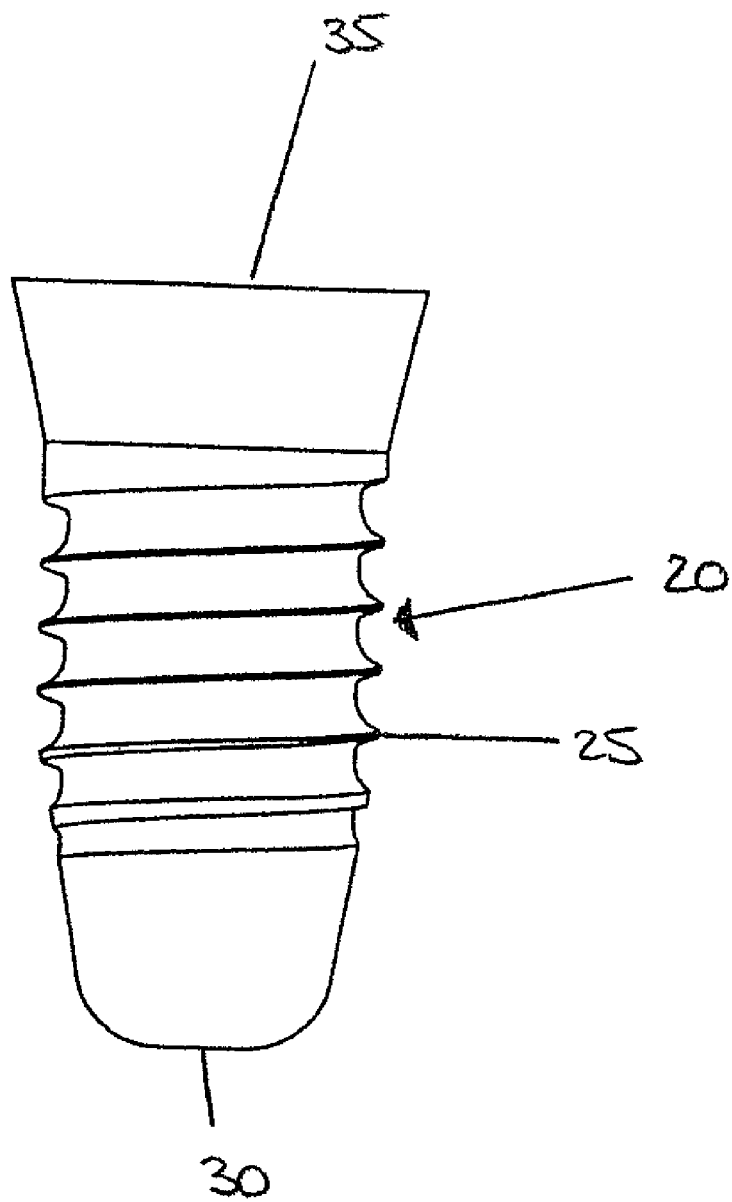
FIG. 3 is a perspective view of a screw implant.

FIG. 3 is a perspective view of a typical screw implant 20 which is intended for connection with an abutment according to the present invention, such as abutments as shown in FIGS. 1 and 2. Said implant has a threaded section 25 und a rounded lower end 30. At the top it is provided with a receiving hole 35 for an abutment. The implant 20 may be made of titanium, zirconium, tantalum, niobium, hafnium or alloys thereof as well as chemically similarly reacting alloys. Alternatively it may be made of ceramic, preferably of zirconium oxide. In order to obtain a good osteointegration the surface of said implant 20 is roughened and preferably also hydroxylated and hydrophilic. If the implant 20 is submerged at bone level, it is surrounded by bone tissue.

The Examples which follow illustrate the invention.

Example 1

Abutment with a Roughened Hydroxylated Soft Tissue Contact Surface

A common shape of an abutment was produced. The soft tissue contact surface was sandblasted with particles having a mean size of 0.25-0.5 mm. The roughened surface was then treated for about five minutes at a temperature above 80° C. with an aqueous hydrochloric acid (conc.)/sulfuric acid (conc.) mixture having an $HCl:H_2SO_4:H_2O$ ratio of 2:1:1. The abutment formed in this way was washed with pure water and then heat-sealed directly in a glass ampoule filled with pure water containing 150 mM $Na^+$ ions, and the corresponding amount of $Cl^-$ anions.

Example 2

Abutment with a Smooth Hydroxylated Soft Tissue Contact Surface

A common shape of an abutment was produced. The soft tissue contact surface was electropolished. The smooth surface was then treated for about five minutes at a temperature above 80° C. with an aqueous hydrochloric acid (conc.)/sulfuric acid (conc.) mixture having an $HCl:H_2SO_4:H_2O$ ratio of 2:1:1. The abutment formed in this way was washed with pure water and then heat-sealed directly in a glass ampoule filled with pure water containing 150 mM $Na^+$ ions, and the corresponding amount of $Cl^-$ anions.

The invention claimed is:

1. Abutment of a dental implant system, the abutment comprising a support region for receiving a prosthetic build-up construction and an implant contact region intended for insertion into a receiving hole of an implant, wherein the abutment comprises between the support region and the implant contact region a soft tissue contact surface comprising a metal, a metal alloy, or a ceramic selected from zirconia, alumina, silica, and mixtures thereof, wherein the soft tissue contact surface is at least partially hydroxylated by hydroxyl groups and is hydrophilic to promote soft tissue attachment.

2. Abutment according to claim 1, wherein the soft tissue contact surface is roughened mechanically and/or by acid etching.

3. Abutment according to claim 2, wherein the abutment is titanium or titanium alloy and the soft tissue contact surface is acid etched.

4. Abutment according to claim 1, wherein the surface roughness of the soft tissue contact surface increases towards the support region continuously or stepwise.

5. Abutment according to claim 1, wherein the abutment is made of ceramic.

6. Abutment according to claim 1, wherein the abutment is coated with a ceramic layer.

7. Abutment according claim 1, wherein said abutment is made of titanium, zirconium, tantalum, niobium, hafnium or an alloy thereof.

8. Abutment according to claim 1, wherein the soft tissue contact surface is completely hydroxylated.

9. Abutment according to claim 1, wherein the abutment is titanium or titanium alloy and the soft tissue contact surface is roughened and hydroxylated.

* * * * *